United States Patent
Sheikh-Ali

(10) Patent No.: US 6,645,388 B2
(45) Date of Patent: Nov. 11, 2003

(54) LEUKOCYTE DEPLETION FILTER MEDIA, FILTER PRODUCED THEREFROM, METHOD OF MAKING SAME AND METHOD OF USING SAME

(75) Inventor: Bashir Musse Sheikh-Ali, Duluth, GA (US)

(73) Assignee: Kimberly-Clark Corporation, Neenah, WI (US)

(*) Notice: Subject to any disclaimer, the term of this patent is extended or adjusted under 35 U.S.C. 154(b) by 60 days.

(21) Appl. No.: 09/746,202

(22) Filed: Dec. 19, 2000

(65) Prior Publication Data

US 2001/0042724 A1 Nov. 22, 2001

Related U.S. Application Data

(60) Provisional application No. 60/171,924, filed on Dec. 22, 1999.

(51) Int. Cl.$^7$ .......................... B01D 61/00; B01D 37/00
(52) U.S. Cl. ...................... 210/767; 210/650; 210/651; 210/243; 210/645; 210/504; 210/500.29
(58) Field of Search .................. 210/767, 650–654, 210/500.37, 295, 500.29, 645, 503, 504, 506; 204/627; 428/43, 44

(56) References Cited

U.S. PATENT DOCUMENTS

| | | |
|---|---|---|
| 2,746,607 A | 5/1956 | Hess |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,585,107 A | 6/1971 | Williams |
| 3,692,618 A | 9/1972 | Dorschner et al. |
| 3,849,241 A | 11/1974 | Butin et al. |
| 3,876,738 A | 4/1975 | Marinaccio |
| 3,895,166 A | 7/1975 | Wood |
| 3,961,125 A | 6/1976 | Suminokura et al. |
| 3,979,285 A | 9/1976 | Wegmuller et al. |
| 4,007,113 A | 2/1977 | Ostreicher |
| 4,007,114 A | 2/1977 | Ostreicher |
| 4,162,348 A | 7/1979 | Juzu |
| 4,230,573 A | 10/1980 | Kilty et al. |
| 4,235,764 A | 11/1980 | Dereser |
| 4,238,329 A | 12/1980 | Zievers |
| 4,241,136 A | 12/1980 | Dereser |
| 4,273,892 A | 6/1981 | Rave |
| 4,282,261 A | 8/1981 | Greene |
| 4,288,462 A | 9/1981 | Hou et al. |
| 4,305,782 A | 12/1981 | Ostreicher et al. |
| 4,309,247 A | 1/1982 | Hou et al. |
| 4,321,288 A | 3/1982 | Ostreicher |
| 4,337,154 A | 6/1982 | Fukuchi et al. |

(List continued on next page.)

FOREIGN PATENT DOCUMENTS

| | | |
|---|---|---|
| DE | 19540876 | 5/1997 |
| EP | 0 005 536 B2 | 11/1979 |
| EP | 0 058 978 A2 | 9/1982 |

(List continued on next page.)

OTHER PUBLICATIONS

Wei et al., US 2001/0040136A1, Nov. 15, 2001.*
Billmeyer, Jr., Fred W., "Textbook of Polymer Science", 1962, p. 368–371.

*Primary Examiner*—Joseph Drodge
*Assistant Examiner*—Krishnan Menon
(74) *Attorney, Agent, or Firm*—Steven D. Flack; James B. Robinson

(57) ABSTRACT

A leukocyte depletion filter media includes nonwoven material or microfiber glass which has been coated with a polysaccharide originally containing functionalized side chains capable of crosslinking with each other and the filter media. The leukocyte depletion filter media preferably includes a polysaccharide having a charge density of up to 5 meq/g.

39 Claims, 2 Drawing Sheets

U.S. PATENT DOCUMENTS

| | | |
|---|---|---|
| 4,340,479 A | 7/1982 | Pall |
| 4,340,480 A | 7/1982 | Pall et al. |
| 4,361,619 A | 11/1982 | Forsten et al. |
| 4,366,068 A | 12/1982 | Ostreicher et al. |
| 4,399,245 A | 8/1983 | Kleber et al. |
| 4,415,664 A | 11/1983 | Barszcz et al. |
| 4,431,542 A | 2/1984 | Dingfors et al. |
| 4,431,545 A | 2/1984 | Pall et al. |
| 4,473,474 A | 9/1984 | Ostreicher et al. |
| 4,473,475 A | 9/1984 | Barnes, Jr. et al. |
| 4,473,476 A | 9/1984 | McMillan et al. |
| 4,477,634 A | 10/1984 | Linder et al. |
| 4,523,995 A | 6/1985 | Pall et al. |
| 4,555,313 A | 11/1985 | Duchane et al. |
| 4,594,158 A | 6/1986 | Chong et al. |
| 4,604,205 A | 8/1986 | Ayers |
| 4,604,208 A | 8/1986 | Chu et al. |
| 4,606,824 A | 8/1986 | Chu et al. |
| 4,608,173 A | 8/1986 | Watanabe et al. |
| 4,612,251 A | 9/1986 | Fredenucci et al. |
| 4,617,124 A | 10/1986 | Pall et al. |
| 4,617,128 A | 10/1986 | Ostreicher |
| 4,639,513 A | 1/1987 | Hou et al. |
| 4,645,567 A | 2/1987 | Hou et al. |
| 4,659,475 A | 4/1987 | Liao et al. |
| 4,663,163 A | 5/1987 | Hou et al. |
| 4,673,504 A | 6/1987 | Ostreicher et al. |
| 4,676,904 A | 6/1987 | Schröder |
| 4,701,267 A | 10/1987 | Watanabe et al. |
| 4,702,840 A | 10/1987 | Degen et al. |
| 4,702,947 A | 10/1987 | Pall et al. |
| 4,707,266 A | 11/1987 | Degen et al. |
| 4,708,803 A | 11/1987 | Ostreicher et al. |
| 4,711,792 A | 12/1987 | Long |
| 4,711,793 A | 12/1987 | Ostreicher et al. |
| 4,724,082 A | 2/1988 | Boom |
| 4,731,260 A | 3/1988 | Balding et al. |
| 4,734,208 A | 3/1988 | Pall et al. |
| 4,734,209 A | 3/1988 | Pall et al. |
| 4,737,291 A | 4/1988 | Barnes, Jr. et al. |
| 4,743,418 A | 5/1988 | Barnes, Jr. et al. |
| 4,747,956 A | 5/1988 | Kiniwa |
| 4,765,915 A | 8/1988 | Diehl |
| 4,765,923 A | 8/1988 | Walterick, Jr. |
| 4,780,369 A | 10/1988 | Schnabel et al. |
| 4,798,615 A | 1/1989 | Fukuta et al. |
| 4,803,171 A | 2/1989 | Baier et al. |
| 4,810,567 A | 3/1989 | Calcaterra et al. |
| 4,810,576 A | 3/1989 | Gaa et al. |
| 4,833,011 A | 5/1989 | Horimoto |
| 4,853,431 A | 8/1989 | Miller |
| 4,859,340 A | 8/1989 | Hou et al. |
| 4,876,036 A | 10/1989 | Candau et al. |
| 4,888,115 A | 12/1989 | Marinaccio et al. |
| 4,895,685 A | 1/1990 | Honda et al. |
| 4,908,137 A | 3/1990 | Chen et al. |
| 4,915,839 A | 4/1990 | Marinaccio et al. |
| 4,923,620 A * | 5/1990 | Pall |
| 4,925,572 A | 5/1990 | Pall |
| 4,936,998 A | 6/1990 | Nishimura et al. |
| 4,944,879 A | 7/1990 | Steuck |
| 4,946,603 A | 8/1990 | Laugharn et al. |
| 4,950,549 A | 8/1990 | Rolando et al. |
| 4,981,591 A | 1/1991 | Ostreicher |
| 5,004,543 A | 4/1991 | Pluskal et al. |
| 5,039,787 A | 8/1991 | Tanaka et al. |
| 5,049,275 A | 9/1991 | Gillberg-LaForce et al. |
| 5,049,282 A | 9/1991 | Linder et al. |
| 5,059,654 A | 10/1991 | Hou et al. |
| 5,085,780 A | 2/1992 | Ostreicher |
| 5,085,784 A | 2/1992 | Ostreicher |
| 5,089,134 A | 2/1992 | Ando et al. |
| 5,091,102 A | 2/1992 | Sheridan |
| 5,094,749 A | 3/1992 | Seita et al. |
| 5,106,501 A | 4/1992 | Yang et al. |
| 5,114,585 A | 5/1992 | Kraus et al. |
| 5,128,041 A | 7/1992 | Degen |
| 5,133,878 A | 7/1992 | Gsell et al. |
| 5,137,633 A | 8/1992 | Wang |
| 5,151,189 A | 9/1992 | Hu et al. |
| 5,160,627 A | 11/1992 | Cussler et al. |
| 5,178,766 A | 1/1993 | Ikeda et al. |
| 5,186,835 A | 2/1993 | Masuoka et al. |
| 5,202,025 A | 4/1993 | Onishi et al. |
| 5,209,849 A | 5/1993 | Hu et al. |
| RE34,296 E | 6/1993 | Roesink et al. |
| 5,227,481 A | 7/1993 | Tsai et al. |
| 5,234,991 A | 8/1993 | Tayot et al. |
| 5,269,931 A | 12/1993 | Hu et al. |
| 5,277,812 A | 1/1994 | Hu et al. |
| 5,288,403 A | 2/1994 | Ohno |
| 5,292,439 A | 3/1994 | Morita et al. |
| 5,298,165 A | 3/1994 | Oka et al. |
| 5,344,560 A | 9/1994 | Surgo et al. |
| 5,344,620 A | 9/1994 | Reiners et al. |
| 5,346,725 A | 9/1994 | Targosz |
| 5,350,443 A | 9/1994 | von Blücher et al. |
| 5,350,523 A | 9/1994 | Tomoi |
| 5,393,379 A | 2/1995 | Parrinello |
| 5,407,581 A | 4/1995 | Onodera et al. |
| 5,425,877 A | 6/1995 | Knappe |
| 5,436,068 A | 7/1995 | Kobayashi et al. |
| 5,438,127 A | 8/1995 | Woodard et al. |
| 5,439,564 A | 8/1995 | Shimizu et al. |
| 5,456,843 A | 10/1995 | Koenhen |
| 5,460,945 A | 10/1995 | Springer et al. |
| 5,472,600 A | 12/1995 | Ellefson et al. |
| 5,494,744 A | 2/1996 | Everhart |
| 5,503,745 A | 4/1996 | Ogata et al. |
| 5,510,004 A | 4/1996 | Allen |
| 5,531,893 A | 7/1996 | Hu et al. |
| 5,543,054 A | 8/1996 | Charkoudian et al. |
| 5,547,576 A | 8/1996 | Onishi |
| H1613 H | 11/1996 | Espy |
| 5,571,657 A | 11/1996 | Szmanda et al. |
| 5,575,892 A | 11/1996 | Devore et al. |
| 5,578,243 A | 11/1996 | Mazaki et al. |
| 5,618,622 A | 4/1997 | Gillberg-Laforce et al. |
| 5,643,375 A | 7/1997 | Wilfong |
| 5,647,985 A | 7/1997 | Ung-Chhun et al. |
| 5,650,479 A | 7/1997 | Glugla et al. |
| 5,652,050 A | 7/1997 | Pall et al. |
| 5,665,235 A | 9/1997 | Gildersleeve et al. |
| 5,679,248 A | 10/1997 | Blaney |
| 5,688,588 A | 11/1997 | Cotton et al. |
| 5,709,798 A | 1/1998 | Adiletta |
| 5,711,878 A | 1/1998 | Ogata et al. |
| 5,714,073 A | 2/1998 | Pall et al. |
| 5,721,031 A | 2/1998 | Echigo et al. |
| 5,736,051 A | 4/1998 | Degen et al. |
| 5,738,788 A | 4/1998 | Tokiwa et al. |
| 5,743,940 A | 4/1998 | Sugo |
| 5,762,797 A | 6/1998 | Patrick et al. |
| 5,776,353 A | 7/1998 | Palm et al. |
| 5,783,094 A | 7/1998 | Kraus et al. |
| 5,785,844 A | 7/1998 | Lund et al. |
| 5,795,483 A | 8/1998 | Ung-Chhun et al. |
| 5,830,367 A | 11/1998 | Gadsby |
| 5,846,438 A | 12/1998 | Pall et al. |
| 5,855,788 A | 1/1999 | Everhart et al. |
| 5,858,503 A | 1/1999 | Everhart et al. |

| | | | | | | |
|---|---|---|---|---|---|---|
| 5,863,654 A | 1/1999 | Frey et al. | | JP | 63-310602 A | 12/1988 |
| 5,869,152 A | 2/1999 | Colon | | JP | 1-199614 A | 8/1989 |
| 5,882,517 A | 3/1999 | Chen et al. | | JP | 1-201582 A | 8/1989 |
| 5,895,575 A | 4/1999 | Kraus et al. | | JP | 1-224004 A | 9/1989 |
| 5,906,724 A * | 5/1999 | Sammons | | JP | 1-224009 A | 9/1989 |
| 5,954,962 A | 9/1999 | Adiletta | | JP | 2-187136 A | 7/1990 |
| 5,958,989 A | 9/1999 | Wang et al. | | JP | 2-212527 A | 8/1990 |
| 5,979,670 A | 11/1999 | Ditter et al. | | JP | 3-293008 A | 12/1991 |
| 5,980,709 A | 11/1999 | Hodges et al. | | JP | 4-029729 A | 1/1992 |
| 6,045,694 A | 4/2000 | Wang et al. | | JP | 4-029730 A | 1/1992 |
| 6,274,041 B1 * | 8/2001 | Williamson et al. ........ 210/243 | | JP | 4-035728 A | 2/1992 |
| | | | | JP | 4-284853 A | 10/1992 |

FOREIGN PATENT DOCUMENTS

| | | | | | |
|---|---|---|---|---|---|
| EP | 0 077 633 A2 | 4/1983 | JP | 9-235399 A | 9/1997 |
| EP | 60058221 | 4/1985 | JP | 11-279945 A | 10/1997 |
| EP | 0 252 477 A2 | 1/1988 | JP | 10-279713 A | 10/1998 |
| EP | 0 347 755 A2 | 12/1989 | WO | WO 90/11814 | 10/1990 |
| EP | 0 496 218 A2 | 7/1992 | WO | WO 93/22039 | 11/1993 |
| EP | 0 606 646 B1 | 9/1997 | WO | WO 96/32178 | 10/1996 |
| EP | 0 792 677 A1 | 9/1997 | WO | WO 97/16233 | 5/1997 |
| EP | 0 811 412 A1 | 12/1997 | WO | WO 97/28882 | 8/1997 |
| GB | 2043734 | 10/1980 | WO | WO 97/41960 | 11/1997 |
| JP | 62-007401 A | 1/1987 | WO | WO 98/01208 | 1/1998 |
| JP | 62-083006 A | 4/1987 | WO | WO 98/04335 | 2/1998 |
| JP | 62-289203 A | 12/1987 | WO | WO 98/32705 | 7/1998 |
| JP | 63-031501 A | 2/1988 | WO | WO 00/09797 | 2/2000 |
| JP | 63-049228 A | 3/1988 | ZA | 97/05944 | 4/1998 |

* cited by examiner

LEUKOCYTE DEPLETION FILTER MEDIA, FILTER PRODUCED THEREFROM, METHOD OF MAKING SAME AND METHOD OF USING SAME

This application claims the benefit pf provisional application Ser. No. 60/171,924 filed Dec. 22, 1999.

FIELD OF THE INVENTION

This invention relates to blood filter media and filters made therefrom, methods for making filter media, and methods for filtering leukocytes from blood using filter media.

BACKGROUND OF THE INVENTION

Many blood transfusions are performed each year in the United States and throughout the world. In connection with these transfusions, the drawn blood of a donor is routinely filtered so as to remove much of the leukocyte component. In this regard, donor leukocytes are known to cause adverse reactions to blood transfusion recipients. For example, donor leukocytes can cause Human Leukocyte Antigen formation (HLA sensitization) if a blood recipient is exposed to a large quantity of leukocytes in the donated blood. Leukocytes may also induce graft versus host reactions in the blood recipients. These are serious conditions, especially for immuno-compromised patients. These individuals, such as those suffering from various forms of Leukemia, typically receive multiple blood transfusions each year. Therefore, the risks of being exposed to such adverse reactions are amplified in such individuals.

Additionally, at this time there is no known benefit in transfusing donor leukocytes to a recipient. Human blood typically contains $10^9$ leukocytes per unit (that is approximately 450 mL of blood). A typical transfusion occurrence requires two or more units of blood. Thus, it is not uncommon for a patient to receive as much as $10^{10}$ white cells in a single transfusion episode, if the blood is not filtered to remove the leukocyte component. It should be noted however, that typically whole blood is filtered or treated in various ways (such as by irradiation) in order to prepare it for transfusion.

In the past, if whole blood or one of the blood components was filtered for leukocytes, the filter typically would end up removing a sizable proportion of another useful blood component, such as the platelets, which may also be attracted to the leukocyte filter. Currently, whole blood is first separated into its components before each component is leuko-depleted, that is filtered of leukocytes. These components are principally (a) packed red blood cells (PRBCs), (b) platelet concentrates and (c) non cellular components i.e. plasma. It would therefore be advantageous and efficient to have a means to leuko-deplete whole human blood before separating the blood into its three known major useful components. Once the leukocytes were filtered out, the whole blood itself could then be used as it is in a blood transfusion process, or if required, individual blood components could be used.

As has already been stated, an efficient method for the leuko-depletion of whole human blood requires the ability to selectively remove leukocytes while recovering red blood cells, platelets and plasma. Typical blood filters rely on mechanical sieving provided by a gradient of the porosity of the filter medium. Centrifugation is also used to separate blood components with different specific gravities. It would also be very desirable if one could use specific interactions between leukocytes and the filter medium to selectively remove the white blood cells from the blood without substantially affecting other cellular components in the blood.

In this regard, there have been three families of adhesion receptors that have been identified for leukocyte rolling, these being the integrins, immunoglobulin-related molecules and selectin molecules. For the purposes of this application, leukocyte rolling means the shear-induced movement of leukocytes that is mediated by adhesion receptors such as integrins and selecting. Integrins are a large family of glycoproteins that attach cells to ligands on surfaces such as those of other cells or surrounding media (for example a filter medium). These receptors have been used to design media that selectively removes leukocytes from whole human blood. Typically, rolling occurs at or below the velocity of the freely flowing cells and in the same direction of the free flowing cells.

In this regard, European Patent Application EP0792677A1 to Haddock provides background on how the adhesion properties of leukocyte surfaces to ligands can be used to design a blood filter that selectively removes leukocytes, while allowing the red cells and the platelets of whole human blood to go through the filter substantially unaffected. Specifically, the application describes how immobilizing carbohydrate ligands such as fucoidan or D-mannose-6-phosphate on functionalized slides enhances binding and aggregation of leukocytes (specifically L-selectins of the leukocytes) on the surface. However, this immobilization method involves functionalizing partially hydrolyzed polyester surfaces with ethylene glycol diglycidyl ether, resulting in epoxy-terminated groups. The epoxy groups are then used to immobilize saccharides in a following step. Such a method involves multiple steps, is laborious and would likely be costly to implement.

Surface treatments such as grafting or coating membranes or nonwoven materials have been used to make filters that are capable of removing leukocytes from whole blood. For example U.S. Pat. No. 4,936,998 to Nishimura et al. discloses a surface coating using acrylic copolymers. Grafting acrylates on surfaces is disclosed in U.S. Pat. No. 4,880,548 to Pall et al. U.S. Pat. No. 5,288,403 to Ohno discloses the use of copolymers containing glucoxyethyl methacrylate coated polyester nonwoven filters with a 99% leukocyte reduction from platelet concentrates. The patent does not discuss the capability of leuko-depleting whole human blood where a large number of red blood cells are present. Also, the described coating is not crosslinked. Consequently there is a risk of potential leaching associated therewith.

U.S. Pat. No. 5,783,094 to Krause et al. discloses coating methods that use a polysaccharide that is claimed to efficiently remove leukocytes from platelet concentrates. These polysaccharides are described as generally water-soluble, and therefore would not likely be suitable for filtration of water-based fluids. The patent describes the further use of a melamine, a cancer suspect/irritant agent, as a secondary crosslinking agent. The efficiency of the filters is described to be in the range of 2+ log reduction for leukocytes, only when non-crosslinked material is used. When crosslinked, the leukocyte depletion efficiency drops below 2 logs, which is traditionally unacceptable for blood transfusions.

U.S. Pat. No. 5,895,575, also to Krause et al., uses the same approach for developing platelet and whole blood filters. Again, non-crosslinked filters show remarkable efficiency, but with the danger of leaching and contaminating the blood. When filters with the crosslinked polysaccharide coating are used, leukodepletion efficiency of whole blood remains high but with slow filtration rates.

Thus, despite the availability of processes to filter leukocytes from whole blood, there is still a need for a filtration process and filter for filtering whole blood of leukocytes, which achieves at least a 3 log leukocyte reduction. Further, there is a need for such a filter which achieves no leaching of the filter coating (i.e. that is crosslinked and has the ability to withstand a thorough wash), and a filtration rate that allows filtration of a unit of blood to be completed within an acceptable time frame. In this regard, a typical bedside transfusion is completed in a period of sixty to one hundred and twenty minutes per unit of blood.

There is also a need for the use of safe crosslinking agents rather than cross linking agents with potentially negative health ramifications which may add additional possibility of danger of a reactive chemical leaching into the transfused blood. Further, there is also a need for blood filter coatings utilizing a crosslinking process that is intramolecular, i.e., the polymer used to coat the substrate is a self-crosslinking one. Finally, there is a need for a highly porous filtration system that contains only nonwoven materials with porosity greater than the largest cellular material in the blood. If such a system would exhibit high leukocyte depletion efficiency without clogging, it would provide an added advantage over membrane (film)-based filter media because a unit of blood would be capable of being filtered and transfused to a patient within a relatively short time period.

SUMMARY OF THE INVENTION

A leukocyte depletion filter media includes a nonwoven or microfiber glass material substrate, which has been coated with a polysaccharide, originally containing functionalized side chains capable of crosslinking with each other and the substrate. It is theorized that receptors on the white blood cells are attracted to ligands in the polysaccharide coating. A microfiber glass substrate may be used as a substrate providing it demonstrates a pore size suitable for blood filtration i.e. pore sizes larger than red blood cells.

Also in accordance with the invention, a leukocyte depletion filter includes a fluid intake, a fluid exit and a leukocyte depletion filter media including a nonwoven material or microfiber glass material which has been coated with a polysaccharide originally containing functionalized side chains capable of crosslinking with each other and filter media situated between said fluid intake and said fluid exit.

Further a method for manufacturing a leukocyte depletion filter media includes the steps of a) preparing a filter media of a nonwoven or microfiber glass material, b) making the filter media wettable, if it is not already so, c) coating the media with a polysaccharide having functionalized side groups capable of crosslinking, and d) heating the filter media so as to cause the functionalized side groups in the coating to crosslink. In an alternative embodiment, the polysaccharide may include a charge density of up to 5 milli-equivalent/gram (meq/g).

A method of filtering leukocytes from whole blood is also disclosed which includes the steps of a) obtaining a unit of whole blood, b) passing the whole blood through a leukocyte depletion filter including a filter media that has been coated with a polysaccharide originally having functionalized side groups capable of crosslinking, such that the whole blood is substantially filtered of leukocytes within 15 minutes.

DETAILED DESCRIPTION OF THE INVENTION

Figure 1:
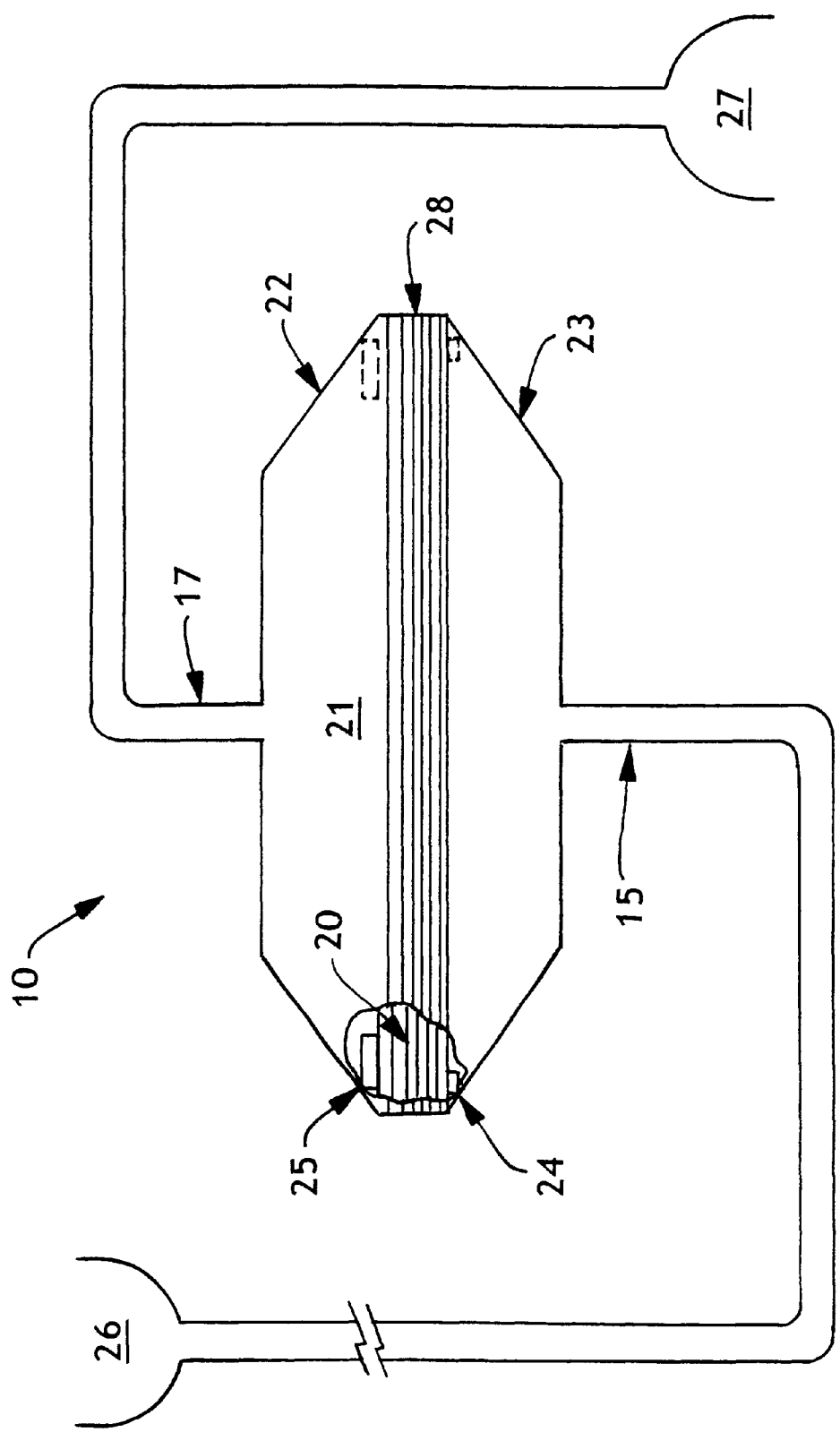
FIG. 1 is a cross-sectional view of a filter in accordance with the invention.

Definitions:

As used herein, the terms "cationically charged" in reference to a coating on a filter fiber and "cationic" in reference to the functionalized polymer mean the presence in the respective coating and polymer of a plurality of positively charged groups. Thus, the terms "cationically charged" and "positively charged" are synonymous. Such positively charged groups typically will include a plurality of quaternary ammonium groups, but they are not necessarily limited thereto.

The term "functionalized" is used herein to mean the presence in the cationic polymer of a plurality of functional groups, other than the cationic groups, which are capable of crosslinking when subjected to heat. Thus, the functional groups are thermally crosslinkable groups. Examples of such functional groups include epoxy, ethylenimino, episulfido, and unblocked siloxane groups. These functional groups readily react with other groups typically present in the cationic polymer. Such other groups typically have at least one nucleophile and are exemplified by amino, hydroxy, and thiol groups. It may be noted that the reaction of a functional group with another group often generates still other groups, which are capable of reacting with functional groups. For example, the reaction of an epoxy group with an amino group results in the formation of a $\beta$-hydroxyamino group. Further, these functional groups may react with other groups on a substrate to crosslink.

Thus, the term "functionalized cationic polymer" is meant to include any polymer which contains a plurality of positively charged groups and a plurality of functional groups which are capable of being crosslinked intramolecularly and possibly with groups on a substrate, by the application of heat.

As used herein, the term "thermally crosslinked" means the coating of the functionalized cationic polymer has been heated at a temperature and for a time sufficient to crosslink the above-noted functional groups. Heating temperatures typically may vary from about 50° C. to about 120° C., but may run as high as 180° C. Heating times in general are a function of temperature and the type of functional groups present in the cationic polymer. For example, heating times may vary from less than a minute to about 60 minutes or more, with times less than 30 minutes being desirable, especially for cationic starch materials such as Co-Bond™ 2500.

As used herein, the term "nonwoven web" means a polymeric web having a structure of individual fibers or threads which are interlaid, but not in an identifiable, repeating manner as in a knitted web. Nonwoven webs have been, in the past, formed by a variety of processes such as, for example, meltblowing processes, spunbonding processes, hydroentangling, air-laid and bonded carded web processes. The basis weight of nonwoven webs is usually expressed in ounces of material per square yard (osy) or grams per square meter (gsm) and the fiber diameters useful are usually expressed in microns. It should be noted that to convert from osy to gsm, multiply osy by 33.91.

As used herein the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown (which will be referred to herein as MB) fibers are carried by the high velocity gas stream and are deposited on a collecting surface to form a web of randomly disbursed MB fibers. Such a process is disclosed, in various patents and publications, including NRL Report 4364, "Manufacture of Super-Fine Organic Fibers" by B. A. Wendt, E. L. Boone and D. D. Fluharty; NRL Report 5265,"An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al., the contents of the patent being incorporated herein by reference. Melt-blown fibers are microfibers, which may be continuous or discontinuous, are generally smaller than 10 microns in average diameter, and are generally tacky when deposited onto a collecting surface.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of the patents being incorporated herein by reference.

As used herein the term "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier et al., U.S. Pat. No. 5,145,727 to Potts et al., U.S. Pat. No. 5,178,931 to Perkins et al., and U.S. Pat. No. 5,188,885 to Timmons et al., each of these patent being incorporated herein by reference. Such a laminate may be made by sequentially depositing onto a moving forming belt first a spunbond fabric layer, then a meltblown fabric layer and last another spunbond layer and then bonding the laminate such as through adhesive or thermal bonding. Thermal bonding typically involves passing a web to be bonded between a heated calender roll and an anvil roll. The calender roll is usually, though not always, patterned in some way so that the entire web is not bonded across its entire surface, and the anvil roll is typically flat. Typically the percent bonding area varies from around 10% to around 30% of the area of the web laminate. As is well known in the art, this type of bonding, sometimes referred to as thermal point bonding, holds the laminate layers together as well as imparts integrity to each individual layer by bonding filaments and/or fibers within each layer.

The fabric layers of a multilayer laminate may alternatively be made individually, collected in rolls, and combined in a separate bonding step. Such fabrics usually have a basis weight of from about 0.1 to 12 osy (6 to 400 gsm). Multilayer laminates may also have various numbers of meltblown layers or multiple spunbond layers in many different configurations.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath-core arrangement wherein one polymer is surrounded by another or a side-by-side arrangement, a pie arrangement, or an "islands-in-the-sea" arrangement. Bicomponent fibers are taught in U.S. Pat. Nos. 5,108,820 to Kaneko et. al., 5,336,552 to Strack et al., and 5,382,400 to Pike et al. which are incorporated herein by reference. The component polymers may be present in any desired ratio. For instance, for two component fibers, the composition of the bicomponent materials may be 50/50 weight/weight polypropylene/polyethylene. Additional ratios include a 75/25 and 25/75 ratio.

As used herein, the term "through-air bonding" or "TAB" means a process of bonding a nonwoven bicomponent fiber web in which air, which is sufficiently hot to melt one of the polymers of which the fibers of the web are made, is forced through the web. The air velocity is between 100 and 500 feet per minute and the dwell time may be as long as 6 seconds. The melting and resolidification of the polymer provides the bonding. Through-air bonding has relatively restricted variability and since through-air bonding requires the melting of at least one component to accomplish bonding, it is restricted to webs with two components like conjugate fibers or those, which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web. An example of through air bonding is described in U.S. Pat. No. 5,667,562 to, David Midkiff, which is incorporated herein by reference.

The term "zeta potential" (also known as "electrokinetic potential") is used herein to mean the difference in potential between the immovable liquid layer attached to the surface of a solid phase and the movable part of the diffuse layer in the body of the liquid. The zeta potential may be calculated by methods known to those having ordinary skill in the art. See, by way of example, Robert J. Hunter, "Zeta Potential in Colloid Science," Academic Press, New York, 1981; note especially Chapter 3, "The Calculation of Zeta Potential," and Chapter 4, "Measurement of Electrokinetic Parameters." In the absence of sufficiently high concentrations of electrolytes, positively charged surfaces typically result in positive zeta potentials and negatively charged surfaces typically result in negative zeta potentials. When an electrolyte solution is forced, by external pressure, through a porous plug of material, a streaming potential develops. The development of this potential arises from the motion of ions in the diffusion layer. This streaming potential is measured with a Brookhaven-Paar BI-EKA instrument and its value is used to calculate the zeta potential. In this measurement, the glass or nonwoven samples are cut to size, 120 mm×50 mm, to fit inside the sample cell. Ag/AgCl electrodes are mounted at each end of the sample cell to measure the streaming potential.

As stated earlier, the present invention provides a leukocyte depletion filter media and filter produced therefrom, a method of making the filter media and a method of using the filter media. The filter media and subsequently produced filter is capable of removing 99.9% of white blood cells (leukocytes) from whole human blood and with a 99% recovery of red blood cells.

The filter 10 (not shown to scale) includes a fluid intake 15, a fluid exit 17, and a filter media 20 desirably contained within a cylindrical filtration chamber 21, as seen in FIG. 1. Desirably the filtration chamber 21 consists of a filter holder of two screwed together halves 22 and 23 (closed along threads 28), and includes a sealing mechanism, such as an "O" ring 24, and/or a teflon washer 25 in order to maintain the filter media secure within the filtration chamber. The filter receives fluid from a reservoir 26 and directs filtered fluid to a collector 27 for eventual usage. The filter desirable uses gravity to move the fluid through its structure, although alternatively, pressure may be used to enhance fluid flow.

The filter media 20 is desirably comprised of layers of coated nonwoven materials such as meltblown material, with gradient porosity from a high of approximately 100 μm (prefilter material) to a low of about 14 μm (filter material). The layers are desirably held together without bonding, in a filter holder, by pressure at their edges, so as to prevent the lateral movement of fluid through the filter 10. Other nonwoven web materials for use in the filter media include spunbonded fibrous webs, multilayered nonwoven web laminates, and conjugate fiber webs. The filter holder is desirably made from a transparent material, such as polystyrene so as to enable the observation of fluid movement and prevent lateral flow. The filter media layers are treated such that leukocytes adhere to their surfaces. Alternatively, in lieu of nonwoven materials, the filter media may comprise microfiber glass material.

The high end of the gradient porosity serves as a pre-filter for removing gel particulates that may form in blood that is kept for any significant amount of time. This prefilter allows for filtration of slightly aged blood units within a relatively short time frame when a surface area of approximately 70 $cm^2$ is used. Such a filter surface may be used to filter a unit of blood in approximately fifteen minutes through gravity. For the purposes of this application the term "unit" shall refer to the standard measurement for a quantity of blood of 450 mL. Desirably, the surface area of the filter is between about 0.5 and 30 $inch^2$ (about 3 to about 200 $cm^2$). Desirably, the number of filter layers is between about 10 and 35 for a total filter basis weight of about 850 to 1500 grams per square meter (gsm). Each layer is typically about 34 gsm in basis weight. Such a filter is capable of a 3-log reduction of leukocytes from whole blood and does not require a separate filtration step for each component of the blood.

The nonwoven materials making up the filter media may be chosen from a variety of available materials including but not limited to, polyester, nylon and polyolefins such as polypropylene that are first made hydrophilic (wettable), such as by treating them with milk protein. Such milk protein may be obtained from powdered skim milk available from grocery stores. Other wetting agents include for example, hydrophilic polymers such as polyvinyl alcohol (PVOH), polyethyleneoxide (PEO), food grade surfactants such as T-AMZ 80K available from the BASF Corporation, and amphiphilic polymers. The nonwoven materials are made wettable so as to allow the functionalized polysaccharide, a charge modifying coating, to adhere to their surfaces. The desirable filter material is any inherently wettable meltblown web, such as a nylon meltblown web. Alternatively, the filter material may be microfiber glass material which, like a nylon meltblown web, is also inherently hydrophilic, and therefore does not need to be made wettable via pretreatment with a wetting agent such as milk protein.

The coating material is desirably a polysaccharide starch with pendent crosslinkable side chains. An example of such a starch is Co-Bond™ 2500 available from National Starch and Chemical Company of Bridgewater, N.J. Such a starch contains functionalized side groups such as unblocked siloxane groups that react intra-molecularly to the hydroxyl groups to form crosslinks with themselves. Alternatively, these unblocked siloxane groups may react with any hydroxyl groups that may be present on a substrate, such as those found on a micro-fiber glass substrate. Such starch is cationically charged, and it is desirable that such starches have a charge density of at least 0.2 meq/g. up to approximately 5 meq/g, more desirably between about 0.5 to about 4 meq/g. While it is not perceived that the attraction of leukocytes to the polysaccharide is based on charge, other detrimental materials may be attracted to the cationic charge and therefore removed by the filter. Co-Bond™ 2500, is particularly effective as a cationic coating in that the charge group is available at the end of a long polymer chain, rather than being buried in the backbone of a polymer chain. Charge modification of the substrate is generally accomplished by coating the substrate or at least some of the fibers with a charge-modifying agent (the starch) and then crosslinking in order to ensure the durability of the coating on the substrate, especially in the presence of water.

As stated earlier, one type of functionalized starch polymer that is particularly suited to this invention is Co-Bond™ 2500 manufactured by National Starch and Chemical Company. Co-Bond™ 2500 is typically sold as a 15% by weight solution of the functionalized starch polymer in water. Co-Bond™ 2500 is a quaternary amine-based starch with unblocked siloxane functionality.

An aqueous solution of functionalized starch polymer is prepared by diluting the functionalized starch solution in water. As a practical matter, the aqueous solution of the functionalized starch polymer typically will include from about 0.1 to about 3.0 percent by weight of the functionalized starch polymer. Desirably, the aqueous solution of the functionalized starch polymer will include from about 0.1 to about 1.0 percent by weight of the functionalized starch polymer. More desirably, the aqueous solution of the functionalized starch polymer will include about 0.4 percent by weight of the functionalized starch polymer.

The advantages such starch provides includes its low cost and ability to further derivatize the side chains and positively affect the substrate surface properties. One such derivitization may be attaching oligo-ethylene glycol or oligo-propylene glycol units to the side chain. This derivitization should enhance the elution of platelets while still maintaining high leuko-depletion efficiency. Further, such starch coatings do not require secondary crosslinking agents to crosslink and therefore do not involve secondary reaction steps or potentially hazardous cross-linking agents. Finally, should such starches leach into the blood filtrate, such materials are not inherently hazardous themselves.

A method is therefore provided for manufacturing a leukocyte depletion filter media which includes the steps of a) preparing a filter media of a nonwoven material, b) making the filter media wettable if it is not already so, and then c) coating the media with a polysaccharide having functionalized side groups capable of crosslinking to each other, and d) heating the filter media so as to cause the functionalized side groups in the coating to crosslink. Desirably the media is coated with such a polysaccharide having a charge density of at least 0.2 to about 5 meq/g, more desirably between about 0.5 and 4 meq/g. Desirably, the filter media is made wettable if necessary, by pretreating it with milk protein.

In an alternate embodiment, a method is provided for manufacturing a leukocyte depletion filter media which comprises the steps of a) preparing a filter media of glass fibers, b) coating the media with a polysaccharide having functionalized side groups capable of crosslinking, and d) heating the filter media so as to cause the functionalized side groups in the coating to crosslink.

A method is also provided for filtering leukocytes from whole blood comprising the steps of a) obtaining whole blood, b) passing the whole blood through a leukocyte depletion filter including a filter media that has been coated with a polysaccharide originally having functionalized side groups capable of crosslinking after heating.

Alternatively, a method is also provided for filtering leukocytes from components of whole blood comprising the steps of a) obtaining whole blood, b) separating the whole blood into useable components, c) passing a useable blood component through a leukocyte depletion filter including a filter media that has been coated with a polysaccharide originally having functionalized side groups capable of crosslinking after heating.

These methods are further described by the examples, which follow. It should be understood that such examples are not meant to be limiting.

Coating Process and Conditions

Pretreating Milk Coating: Since polypropylene meltblown is not wettable, milk protein pretreatment must be done in a forced process. One such process involves (a) passing a 2-wt % skim milk powder in mild water (between about 40 to 70° C.) through the individual non-wettable meltblown filter media until it is all wet by the milk/water solution and (b) drying in air. The process of "passing milk through the non-wettable nonwoven web" may be achieved in at least the following ways: (a) a filtration setting where the fluid is pressed or drawn through the web or in (b) a continuum process where a submerged vacuum or pressure orifices force the milk solution to pass through the web and, in the process, coats a moving web. Upon passing the milk solution through the polypropylene meltblown and air drying it, the medium becomes instantaneously wettable by water. Desirably a 0.5–5-weight % skim milk in deionized water is typically used for this process. It should be recognized that if nylon meltblown, glass fibers, or other inherently wettable material is used as the filter media, the milk pretreatment is not necessary.

In the examples a 0.1–2 weight % aqueous solution of polysaccharide coating polymer was used throughout. Approximately 0.4 weight % is a desirable polysaccharide coating composition. Three specific types of comparative coating chemistries were used in the examples. In the first type, a 0.4 weight % Kymene 450® solution from Hercules Inc., of Wilmington, Del., was filtered through individual layers of the filter, air dried at a room temperature of approximately 25° C., and then baked in an air circulated oven at 85° C. for about one hour. The filter material was then thoroughly washed with de-ionized water at approximately 25° C and air dried at approximately 25° C. for 16 hours.

In the second type of coating, an aqueous solution containing 0.2% water-soluble starch (hydrolyzed potato starch obtained from Aldrich Chemical Company) and 0.2 weight % Kymene 450® was used. The rest of the process was the same as in the type 1 coating description.

The third type of coating was 0.4 weight % aqueous solution of Co-Bond™ 2500 (National Starch). In this type of coating, the coating solution was passed through individual filter layers by suction or pressure filtration. The filter media was then air-dried for 16 hours at a temperature of approximately 25° C. and then baked at 105° C. for about thirty minutes in an air-circulated oven. Following baking, the filter media was thoroughly washed with de-ionized water and again air-dried at approximately 25° C. for 24 hours. Alternatively, other coating methods could have been used, where the coating solution is forced through the web, the web is nipped of excess coating, air dried, baked, cut to pieces, washed with de-ionized water, and then air dried at the previously stated temperatures and time frames.

Filter Media and Prefilters

A filter unit desirably includes a number of layers of prefilters and filters. The filter layers are placed down stream with respect to the prefilters. For example, if the blood bath flow is from top to bottom, the prefilters are placed over the filter layers. Conversely, if the filtration path of the blood is from bottom to top, the prefilters are placed underneath the filters. Irrespective, the prefilters and filters are arranged such that the blood first goes through the prefilters, followed by the filter layers. It is desirably that gravity be used to move the blood flow through the filter system, although the blood can be forced through the filter system by active pressure or vacuum.

In the examples, the polypropylene and nylon 6 meltblown filters and polyolefin nonwoven prefilters were all obtained from the Kimberly-Clark Corporation. The polypropylene meltblown used had a typical basis weight of 34 gsm. Initially polypropylene meltblown filter media was used, but this was changed to nylon meltblown because of the higher wettability afforded by nylon webs when compared to polypropylene webs. Also, since nylon webs are inherently wettable, their use simplifies the coating process from two successive coatings (pretreatment of milk-coating to make wettable, followed by other coating layer for polypropylene webs) to a single coating step (for nylon webs).

Typically, the nylon meltblown filter fabric used had a basis weight of between about 34 to 85 grams per square meter. In particular, a 34 gsm with an apparent density of 0.18 g-cm$^{-3}$ has been shown to be an effective filter medium. Higher basis weights in individual filter layers may be used, but typically result in tighter pore-sizes and resultant reduction of flow rate of the fluid to be filtered. Lower basis weight may also be used but with less efficiency, making it necessary to increase the basis weight of the total filter unit higher than the desired 850–1500 gsm range. A basis weight of 850–1500 gsm is desired because desired leuko-depletion is difficult to achieve with filter media having lower than about 850 gsm total basis weight, while using higher basis weight filter media increases the amount of blood that gets entrapped during filtration. Thus, it is desirable to use only the amount of filter media necessary to provide the desired 3-log reduction of leukocytes while minimizing the amount of blood clogged/entrapped in the filter. Desirably, a 1000 to 1200 gsm basis weight filter media in accordance with the present invention, made of 34 to 50 gsm individual layers provides leuko-depletion efficiency of 99.9%, and at a filtration rate of about fifteen minutes per unit of blood.

Three types of prefilters were used in the examples, which follow. The first was a meltblown with low basis weight such that the average pore sizes are reasonably high to be effective prefilters. In particular, a 17-gsm polypropylene meltblown with average pore size of about 45 μm was proven to be an effective pre-filter. The second type of prefilter used was a spunbond-meltblown-spunbond (SMS) tri-layer nonwoven fabric, also available from Kimberly-Clark Corporation. The average pore size of this prefilter was similar to that of the layer with the lowest average pore size, namely the meltblown middle layer. However, the spunbond layer provided some depth filtration capability, which makes the prefilter effective at removing gels in the blood. In particular the meltblown layer of the SMS was made of polypropylene and the spunbond was made from 50/50 bicomponent polypropylene/polyethylene in a side by side arrangement. The third type of prefilter material used was a 100-gsm, through-air bonded bicomponent spunbond layer with average pore sizes of 44 µm and an apparent density of 0.11 $g\text{-}cm^{-3}$. Such material is available under the designation Breeze®, although any through air bonded bicomponent spunbond material with an approximately 3 osy basis weight and similar porosity should suffice. The bicomponent spunbond layer was made from 50/50 polypropylene and polyethylene in a side by side arrangement, and was also manufactured by the Kimberly-Clark Corporation. This prefilter proved to be very effective. A layer of this prefilter coupled with 32 layers of 34-gsm Nylon 6 meltblown with average pore size of 14 µm and coated with crosslinkable starch proved to be a desirable embodiment.

Test Procedures

Coating Process Summary

Circular disks with 3 inch diameter were die-cut and placed in a buchner funnel on a filtering flask. The sample was first wetted with deionized water so that when the house vacuum is applied on the filtering flask, it sets firmly on the perforated surface of the buchner funnel. A 1-L solution (milk or other coating chemistries) was poured at a rate higher than the controlled suction rate so that the whole sample was immersed in the solution at least for a few seconds of the filtration time. The whole filtration was completed in 30 seconds.

Alternatively, the sample may be pre-wet with the coating solution, placed in the buchner funnel, have the house vacuum applied and the remainder of the solution poured on the sample such that it is filtered through. After the liquid is completely filtered through, the vacuum is disconnected and the sample removed. The samples are either dried at room temperature (milk-coating case) or transferred into a convection oven for crosslinking (Kymene and Co-Bond cases).

After completion of the crosslinking step, the samples were placed in a buchner funnel on a filtering flask, and washed with deionized water following a procedure similar to that used in the coating step. The objective was to make sure that the whole sample was thoroughly washed. The washed samples were dried at room temperature.

Leukocyte depletion experiments using a Co-Bond™ 2500 coating were conducted by gravity filtering 100 mL of a 2–5 day old unit of blood obtained from the Interstate Blood Bank of Memphis, Tenn. For each of the experiments, the blood was introduced into a filter as in the one generally described in FIG. 1, including the filter media, and a fluid exit.

Typical human blood from a healthy donor contains between about 4,000–12,000 white blood cells per microliter of blood, before filtration using standard leukocyte filtration methodology. The corresponding leukodepleted blood of the current method with 99.9% efficiency, contained 4–10 leukocytes (white blood cells)/µL. A Baker System 9120+ hemocytometer (by BioChem ImmuniSystems Inc., Montreal, Canada) was initially used to perform such calculation/testing using manufacturer recommended operating procedures. The Baker System 9120+ electronically counts white blood cells, red blood cells and platelets by employing the volumetric impedance principle. This principle of electronic counting and sizing uses the difference in ionic conductivity between blood cells and the diluent in which the cellular materials are suspended. The diluent is an electrolyte capable of conducting electricity. The suspension passes through specifically designed apertures where the conductivity of the diluent remains constant as long as cellular material does not pass through the cell. Blood cells are non-conductive and their presence in the circuit is indicated by a momentary increase in resistance. The magnitude of this momentary disturbance is directly proportional to the cell volume. The passing of the cells, signaled by electric pulses, are thus sized and counted. The cell counter discriminates resistance increase produced by different blood cells. Differential lysing techniques, where red blood cells are destroyed, are used to distinguish white cell subpopulations by using the rates at which different white cells shrink in the presence of the lysing reagent. Thus, accurate size data is obtained by using exact dilution and lyse addition timing.

The Baker System 9120+ has a lower detection limit (referred as LDL) of 100 cells per microliter. The LDL is the smallest value of analyte that is statistically distinguishable from zero. The Baker instrument was initially used to count white blood cells in leuko-depleted blood until filters with the leuko-depletion efficiency that leads to white blood cell counts lower than the LDL of the instrument were created. Use of the inventive method now produces filters capable of leuko-depleting blood such that white blood cell residuals below the LDL limit of many counting methods are obtainable. However, a technique for counting residual white blood cells from leuko-depleted human blood has been developed using a DNA staining method. This technique is fully described in K. J. Kao & J. C. Scornik, *Transfusion* 20, 774–777 (1989), the text of which is incorporated herein by reference. In this test method, hypotonic propedium iodide (PI) solution is used to stain the nuclear DNA of white blood cells, hereinafter referred to as the PI test method. The hypotonicity and the presence of a surfactant in the staining solution solubilizes the red blood cells and platelets and allows the permeation of PI through the nuclear membrane.

The binding of PI to the nuclear DNA enables the nuclear DNA to fluoresce (bright orange-red) providing an easy method of identification with a fluorescence microscope, even at very low levels of magnification. A green light (obtained using a 480 nm band-pass filter cube) is used as an excitation source and the emission at red region (collected through a 550 nm cut-off filter) is viewed where the white blood cells appear as red dots in a black background. Multi-nuclear cells appear as diffuse while the mononuclear cells appearing as sharp dots.

The hypotonic PI solutions for testing of the blood samples filtered by the inventive method, were made by mixing 5 mg of PI, 100 mg sodium citrate and 30 mL of the detergent NP-40, (from Sigma Chemical Company of St. Louis, Mo.) in 100 mL distilled water. The solutions were filtered through a 0.22 mm Gelman filter obtained from Gelman Sciences, Ann Arbor, Mich. and kept in the dark at approximately 4° C. The solutions were kept for no more than two weeks.

To determine the efficacy of the nuclear labeling method, a series of experiments were conducted to determine white blood cell content of whole human blood that has been diluted successively. To that end, aliquots of blood were diluted with hypotonic solutions using the dilution factors listed in the first column of Table 1, which follows. Table 1 shows the counted white blood cells in serially diluted whole human blood using a hemocytometer and propedium iodide method. The initial white blood cell count of the stock blood was 7200 cells/μL.

TABLE 1

| Dilution Factor | Expected Count* (In 1000 cells/μL) | Hemocytometer Count (in 1000 cell/μL) | PI method Count (in 1000 cells/μL) |
| --- | --- | --- | --- |
| 1 | | 7.2 | |
| 11 | 0.650 | 0.6 | 0.700 |
| 21 | 0.343 | 0.3 | 0.400 |
| 41 | 0.176 | 0.2 | 0.230 |
| 81 | 0.089 | 0.1 | 0.078 |
| 161 | 0.045 | 0 | 0.045 |
| 410 | 0.018 | 0 | 0.016 |

The expected count is based on applying the dilution factor to the starting count of white blood cells in the unit of blood (7200 WBCs/μL) using the following equation:

Expected Count=(WBC count of unfiltered blood)/(dilution factor)

where 'WBC count of unfiltered blood'=7200 cells per microliter for the example given in Table 1 and 'dilution factor' is given in column 1 of Table 1.

The diluted solutions were vortexed for one minute and incubated at room temperature (approximately 25° C.) for fifteen minutes. The mixtures were then loaded in a hemocytometer. Data in the third column of Table 1 was then obtained.

Fifty microliters of the mixture were also loaded on a Naegeotte chamber (i.e., a 50 μL per grid chamber obtained from Hausser Scientific, Horsham, Pa.) and examined on a fluorescence microscope equipped with a 480 nm band pass excitation filter and a 550 nm band pass filter on the viewing lens. The number of WBCs per μL listed in the fourth column of Table 1 was then calculated by counting the number of cells in the Naegeotte chamber and correcting for the volume factor using the following equation:

Number of WBCs per μL=(Average number of WBC in the viewed area of chamber×Magnification Factor×Dilution Factor)/(Grid volume in μL)

where the magnification factor of 1200 was calculated from pictures taken from the magnified chamber grids at the same magnification used in the experiments, and a chamber of 1.5 cm×1.5 cm. The dilution factor is the ratio of filtered blood to the total volume of diluted sample analyzed, after addition of the propedium iodide solution. The dilution factor was typically 9.1 for experiments on filtered blood (i.e., 1 part filtered blood and 10 parts of PI solution). Total WBC was determined with the Baker Systems 9120+ Hemocytometer and typically ranged from 7200 to 10,500 WBCs/μL for different units of blood tested. The volume of each chamber grid (a total of two grids) was 50 μL.

The Leuko-depletion efficiency or WBC reduction % was calculated in accordance with the following equation:

Leuko-depletion Efficiency (%)=100×(WBC count in leuko-depleted blood)/(WBC count of unfiltered blood)

where the counts are per microliter. The number of white blood cells per microliter of unfiltered blood was determined with the Baker System 9120+ and the number of WBCs per microliter leuko-depleted blood was determined using the PI test system. When blood filtered with filter numbers 9 & 10 was measured with the Baker System 9120+, a zero WBC reading was obtained.

Figure 2:
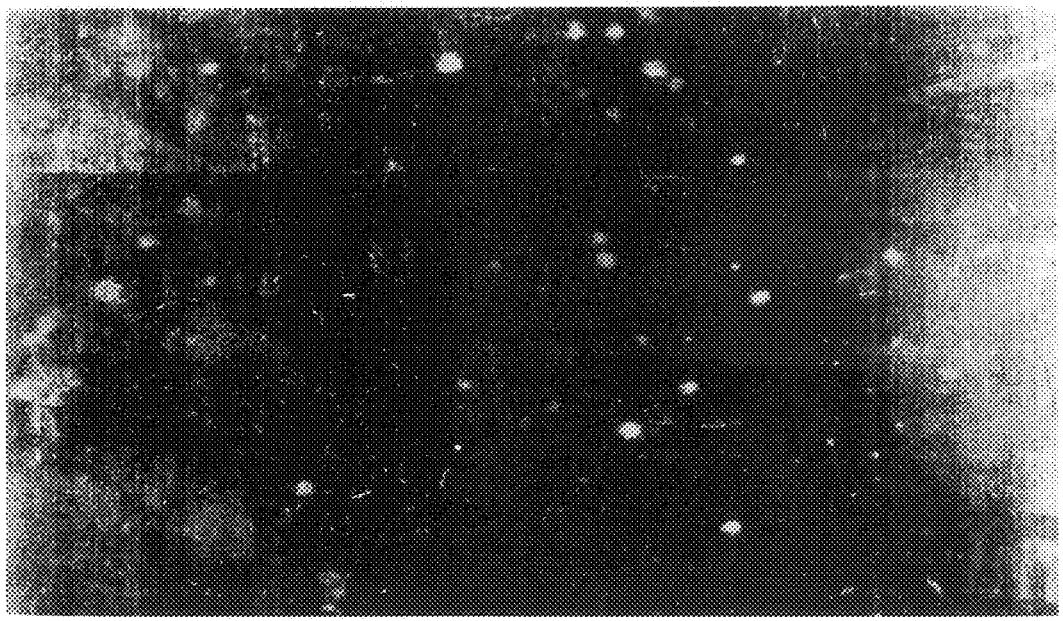
FIG. 2 illustrates hypotonic propedium iodide stained fluorescence of a diluted human blood sample, filtered of leukocytes in accordance with the present invention.

FIG. 2 shows PI stained fluorescence of a diluted human blood sample of the filtration method of the current invention. It can be seen from the image in FIG. 2 that white blood cells are illuminated as gray dots on a black background when shown in a black and white image. Using the nuclear labeling method, residual white blood cells in leuko-depleted human blood of the most effective blood filter was determined (Filter#10).

The present invention is further described by the specific examples which follow. Such examples, however, are not to be construed as limiting in any way either the spirit or the scope of the present invention.

EXAMPLES

The examples are described in detail in Table 2, which follows. Examples 2 and 5 used polypropylene meltblown coated with milk as filter media. Examples 1, 3, and 5–9 used polypropylene meltblown coated first with milk followed by the coating chemistry specified in row 2 of Table 2. Example 10 used Nylon 6 meltblown coated with Co-Bond™ 2500® as filter media. Examples 1 and 2 used no prefilter. Examples 3 and 4 used eight layers of meltblown designation 1102 as a prefilter in addition to the meltblown filters described above. Meltblown designation 1102 is a 17 gsm polypropylene meltblown with average pore sizes of 45 μm, obtained from Kimberly Clark. Examples 5 and 6 used two prefilters in addition to the meltblown filters described above, a first prefilter consisting of four layers of meltblown designation 1102 described above, and a second prefilter consisting of a layer of a spunbond-meltblown-spunbond with depth filtration capability and with pore sizes similar to that of meltblown, of approximately 15 μm. Examples 7–9 used either eight (for examples 7 and 8) or sixteen (for example 9) layers of meltblown designation 1102 described above as prefilters in addition to the meltblown filters. Example 10 used 32 34-gsm nylon meltblown filters and a 100-gsm through-air bonded bicomponent spunbond described above.

TABLE 2

| | Leukocyte Reduction | | | | | | | | | |
| --- | --- | --- | --- | --- | --- | --- | --- | --- | --- | --- |
| Examples | #1 | #2 | #3 | #4 | #5 | #6 | #7 | #8 | #9 | #10 |
| Coating | K | Milk | K | Milk | K | K/S | K | K/S | K/S | CS |
| #Layers | 8 | 8 | 16 | 16 | 24 | 24 | 24 | 24 | 24 | 32 |
| #Layers of SMS Pre-filter | 0 | 0 | 0 | 0 | 1 | 1 | 0 | 0 | 0 | 0 |
| Breeze ® Pre-filter** | 0 | 0 | 0 | 0 | 0 | 0 | 0 | 0 | 0 | 1 |

TABLE 2-continued

| | Leukocyte Reduction | | | | | | | | | |
|---|---|---|---|---|---|---|---|---|---|---|
| Examples | #1 | #2 | #3 | #4 | #5 | #6 | #7 | #8 | #9 | #10 |
| #Layers of MB 1102 Pre-filter | 0 | 0 | 8 | 8 | 4 | 4 | 8 | 8 | 16 | 0 |
| Gsm*** | 270 | 270 | 680 | 680 | 980 | 980 | 950 | 950 | 1085 | 1190 |
| WBC Reduction (%) | 64 | 59 | 97 | 88 | 85 | 97 | 98 | 97 | >98* | 99.9 |
| Volume (mL) | 50 | 50 | 100 | 100 | 100 | 100 | 100 | 100 | 50 | 100 |
| Filtration Time in (minutes) | 15 | 10 | 5 | 4 | 9 | <3 | 10 | 6 | 8 | <3 |

*The detection limit of the instrument
**A 100-gsm, through-air bonded bicomponent spunbond with 44 μm average pore size
***Total Gram per square meter of filter including pre filter The following designations represent the coating used in Table 2. Coatings: K, Kymene® 450; K/S, Kymene 450/soluble starch obtained from Aldrich; CS, Co-Bond™ Starch obtained from National Starch. Milk was a 2 weight % solution of skim milk obtained from the local grocery store.

From the examples it can therefore be seen that cationically charged starch polymers with the capability to crosslink intramolecularly and to crosslink with substrate materials, allow for the formation of efficient leukodepletion filters without the necessity of potentially hazardous secondary crosslinking agents or multiple manufacturing steps.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for manufacturing a leukocyte depletion filter media comprises the steps of:
    a) preparing a filter media of a nonwoven material;
    b) making the filter media wettable if it is non inherently wettable;
    c) coating the media with a cationic polysaccharide having functionalized side groups capable of crosslinking; and
    d) heating the filter media so as to cause the functionalized side groups in the coating to crosslink intramolecularly without the use of a crosslinking agent.

2. The method for manufacturing a leukocyte depletion filter of claim 1 wherein said coating step said polysaccharide includes a charge density of between about 0.2 meq/g to about 5 meq/g.

3. The method for manufacturing a leukocyte depletion filter of claim 2 wherein said coating step said polysaccharide includes a charge density of between 0.5 meq/g and 4.0 meq/g.

4. The method for manufacturing a leukocyte depletion filter media of claim 1 wherein step "a)" the filter media is prepared from a meltblown nonwoven material.

5. The method for manufacturing a leukocyte depletion filter media of claim 1 wherein step "a)" the filter media is prepared from multiple layers of nonwoven material.

6. The method for manufacturing a leukocyte depletion filter media of claim 1 wherein step "a)" the filter media is prepared from at least one prefilter layer and at least one filter layer.

7. The method for manufacturing a leukocyte depletion filter media of claim 1 wherein step "b)" the filter media is made wettable by exposing it to milk protein.

8. A method for manufacturing a leukocyte depletion filter media comprises the steps of:
    a) preparing a filter media of a microfiber glass;
    b) coating the media with a cationic polysaccharide having functionalized side groups capable of crosslinking; and
    c) heating the filter media so as to cause the functionalized side groups in the coating to crosslink intramolecularly without the use of a crosslinking agent.

9. The method for manufacturing a leukocyte depletion filter of claim 8 wherein said coating step said polysaccharide includes a charge density of between about 0.2 and 5 meq/g.

10. The method for manufacturing a leukocyte depletion filter media of claim 8 wherein step a) the filter media is prepared from multiple layers of microfiber glass.

11. The method for manufacturing a leukocyte depletion filter media of claim 8 wherein step a) the filter media is prepared from at least one prefilter layer and at least one filter layer.

12. A method for manufacturing a leukocyte depletion filter media comprises the steps of a) preparing a wettable filter media of a nonwoven material, b) coating the media with a cationic polysaccharide having functionalized side groups capable of crosslinking, and c) heating the filter media so as to cause the functionalized side groups in the coating to crosslink intramolecularly without the use of a crosslinking agent.

13. The method for manufacturing a leukocyte depletion filter of claim 12 wherein said coating step said polysaccharide includes a charge density of between about 0.2 meq/g to about 5 meq/g.

14. The method for manufacturing a leukocyte depletion filter of claim 13 wherein said coating step said polysaccharide includes a charge density of between about 0.5 meq/g and 4.0 meq/g.

15. The method for manufacturing a leukocyte depletion filter media of claim 12 wherein step "a)" the filter media is prepared from a meltblown nonwoven material.

16. The method of manufacturing a leukocyte depletion filter media of claim 15 wherein step "a)" the filter media is prepared from nylon 6.

17. The method for manufacturing a leukocyte depletion filter media of claim 12 wherein step "a)" the filter media is prepared from multiple layers of nonwoven material.

18. The method for manufacturing a leukocyte depletion filter media of claim 17 wherein step "a)" the filter media is prepared from at least one prefilter layer and at least one filter layer.

19. A method of filtering leukocytes form whole blood includes the steps of:
   a) obtaining a unit of whole blood;
   b) passing the whole blood through a leukocyte depletion filter media including a filter media that has been coated with a cationic polysaccharide originally having functionalized side groups capable of crosslinking intramolecularly without the use of a crosslinking agent.

20. The method of filtering leukocytes from whole blood of claim 19 wherein said filter media has been coated with a polysaccharide originally having functionalized side groups capable of crosslinking and including a charge density of up to 5 meq/g.

21. A method of filtering leukocytes form whole blood includes the steps of:
   a) obtaining a unit of whole blood;
   b) separating the desirable blood component from the whole blood; and
   c) passing the desirable blood component through a leukocyte depletion filter media including a filter media that has been coated with a cationic polysaccharide originally having functionalized side groups capable of crosslinking intramolecularly without the use of a crosslinking agent.

22. The method of filtering leukocytes from a blood component of claim 21 wherein said filter media has been coated with a polysaccharide having functionalized side groups capable of crosslinking and including a charge density of up to 5 meq/g.

23. A leukocyte depletion filter comprising:
   a) a fluid intake;
   b) a fluid exit; and
   c) a leukocyte depletion filter media including a nonwoven material which has been coated with a cationic polysaccharide originally containing functionalized side chains capable of crosslinking intramolecularly without the use of a crosslinking agent, said filter situated between said fluid intake and said fluid exit.

24. The leukocyte depletion filter of claim 23 wherein said polysaccharide includes a charge density of up to 5 meq/g.

25. The leukocyte depletion filter of claim 23 wherein said filter media includes multiple nonwoven layers.

26. The leukocyte depletion filter of claim 23 wherein said filter media filters leukocytes to a level of approximately ten leukocytes per microliter as measured by the PI Test Method.

27. The leukocyte depletion filter of claim 23 wherein said filter media filters leukocytes to a level of between approximately four to ten leukocytes per microliter as measured by the PI Test Method.

28. A leukocyte depletion filter comprising:
   a) a fluid intake;
   b) a fluid exit; and
   c) a leukocyte depletion filter media including a microfiber glass material which has been coated with a cationic polysaccharide originally containing functionalized side chains capable of crosslinking intramolecularly without the use of a crosslinking agent, said filter situated between said fluid intake and said fluid exit.

29. The leukocyte depletion filter of claim 28 wherein said filter media includes multiple microfiber glass layers.

30. The leukocyte depletion filter of claim 28 wherein said filter media filters leukocytes to a level of approximately ten leukocytes per microliter as measured by the PI Test Method.

31. The leukocyte depletion filter of claim 28 wherein said filter media filters leukocytes to a level of between approximately four to ten leukocytes per microliter as measured by the PI Test Method.

32. A leukocyte depletion filter media comprising: nonwoven material which has been coated with a cationic polysaccharide originally containing functionalized side chains capable of crosslinking intramolecularly without the use of a crosslinking agent.

33. The leukocyte depletion filter media of claim 32 wherein said nonwoven material includes multiple nonwoven layers.

34. The leukocyte depletion filter media of claim 32 wherein said nonwoven material filters leukocytes to a level of approximately ten leukocytes per microliter as measured by the PI Test Method.

35. The leukocyte depletion filter media of claim 32 wherein said nonwoven material filters leukocytes to a level of between approximately four to ten leukocytes per microliter as measured by the PI Test Method.

36. A leukocyte depletion filter media comprising: a microfiber glass material which has been coated with a cationic polysaccharide originally containing functionalized side chains capable of crosslinking intramolecularly without the use of a crosslinking agent.

37. The leukocyte depletion filter of claim 36 wherein said microfiber glass material includes multiple layers.

38. The leukocyte depletion filter media of claim 36 wherein said microfiber glass material filters leukocytes to a level of approximately ten leukocytes per microliter as measured by the PI Test Method.

39. The leukocyte depletion filter media of claim 36 wherein said microfiber glass material filters leukocytes to a level of between approximately four to ten leukocytes per microliter as measured by the PI Test Method.

* * * * *